United States Patent [19]

Gronsfeld et al.

[11] Patent Number: 4,875,371

[45] Date of Patent: Oct. 24, 1989

[54] DETERMINING IMPURITIES IN SAMPLES

[75] Inventors: Josef Gronsfeld, Toenisvorst; Hatto Jacobi, Duesseldorf; Hans-Jüergen Bäethmann, Moers, all of Fed. Rep. of Germany

[73] Assignee: Mannesmann AG, Duesseldorf, Fed. Rep. of Germany

[21] Appl. No.: 219,764

[22] Filed: Jul. 15, 1988

[30] Foreign Application Priority Data

Jul. 22, 1987 [DE] Fed. Rep. of Germany ....... 3724627
Oct. 23, 1987 [DE] Fed. Rep. of Germany ....... 3736389

[51] Int. Cl.⁴ ............................................. G01N 29/04
[52] U.S. Cl. ......................................... 73/598; 73/863
[58] Field of Search .............. 73/598, 600, 863, 865.8, 73/866; 72/31, 32, 365; 164/4.1

[56] References Cited

U.S. PATENT DOCUMENTS 3,354,699 11/1967 Carnevale et al. ..................... 73/598

Primary Examiner—Jerry W. Myracle
Attorney, Agent, or Firm—Ralf H. Siegemund

[57] ABSTRACT

A sample is cut from the upper region of a continuously cast ingot and rolled to compact the impurity band in a direction that was horizontal during casting.

15 Claims, 12 Drawing Sheets

Fig.5
ORIGINAL: 160:1
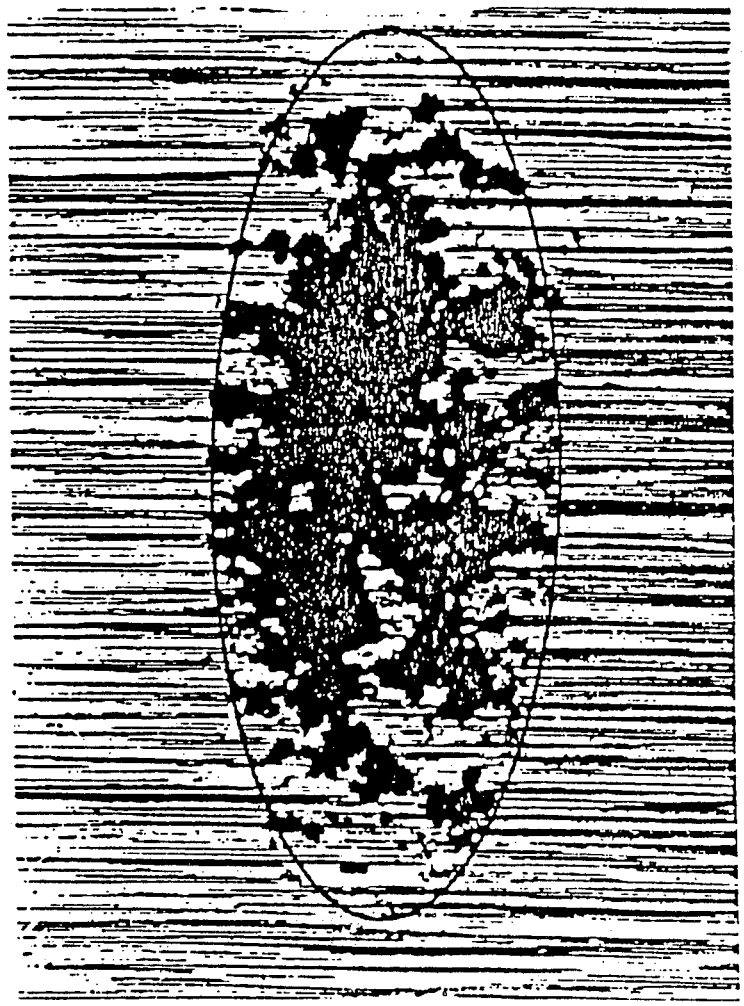

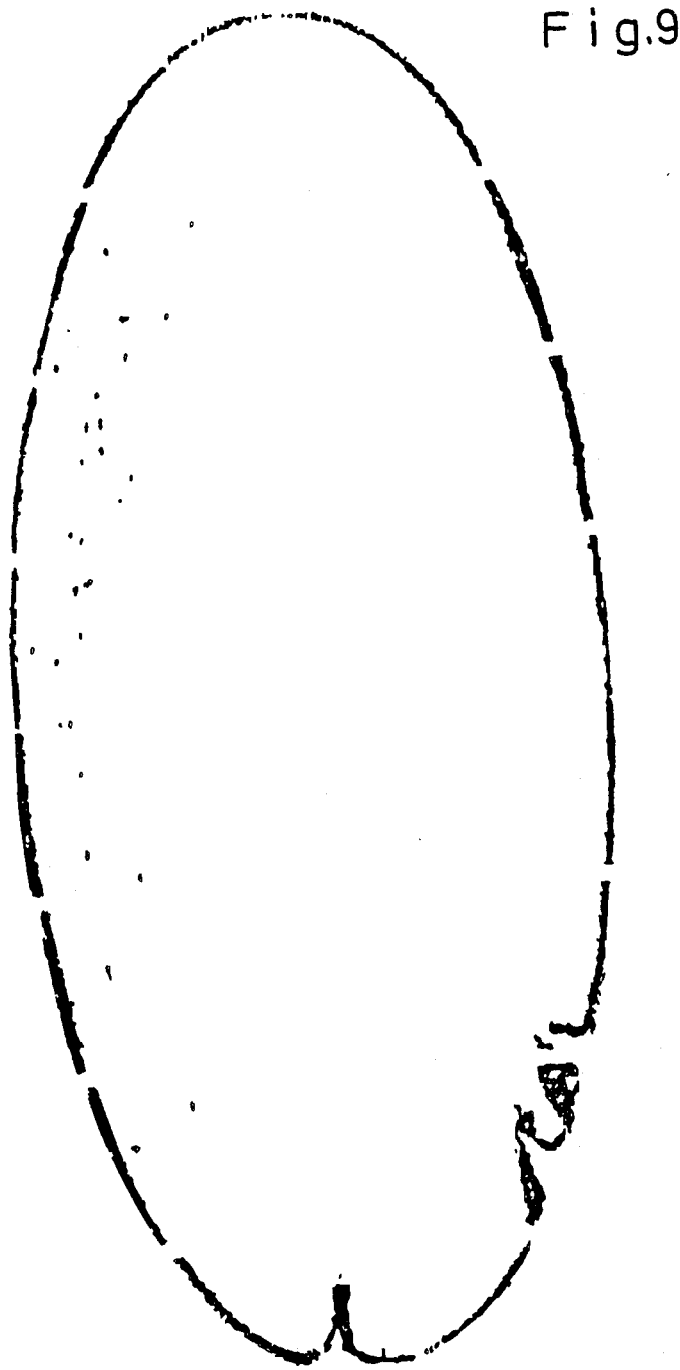
ORIENTATION ROLLING OF UNKNOWN ROUND
PRODUCTION: CAST BLOOM 360 BY 420mm
THEN ROLLED TO 177mm DIAMETER

RETRANSFORMATION (MATHEMATICAL) OF
ULTRASONIC TEST (FIG 9)

ULTRASONIC TEST RESULT OF A ROLLED SLAB
SAMPLE TAKEN FROM UPPER HALF SLAB WIDTH

ULTRASONIC TEST RESULT IN A ROLLED SAMPLE
(UPPER HALF OF SLAB, ADJACENT SMALL SIDE)

DETERMINING IMPURITIES IN SAMPLES

BACKGROUND OF THE INVENTION

The present invention relates to the making of samples for purposes of determining the degree of purity of metals. Within the context of this invention, metal includes iron as well as non-ferous metals and alloys thereof. It is assumed that owing to the particular metalurgical history these metals may contain undesirable impurities. Impurities within this context are essentially non-metallic phases which are deformable depending upon temperature. Their inclusion is presumed to impart undesirable properties upon the metal. It is known to inspect and test metals through ultrasonic processes, and the content of the impurities can be subsequently indicated and evaluated. Generally speaking, these tests are conducted within the frame of determining degrees of impurity.

As far as iron and iron alloys are concerned, the invention finds particular utility in the case of steel having been processed by continuous casting.

It is a general trend to increase requirements on a product, and stringent requirements include the one concerning purity as defined above. Aside from the problem of attaining the desired degree of purity, it is also a problem to determine the degree of purity in the first place. With increasing demands, it was found that standardized test methods of the past are no longer adequately reliable. This means that, to an increasing extent, failure rates of a product, either during manufacture or even on use, become a rather belated indicator of the degree of purity of the metal involved. As far as steel and metallurgical developoments generally are concerned, this is a very undesirable situation. Generally speaking, one can not expect a "feedback" between user and manufacturer, and even if such a feedback exists, say through complaints, a long delay could be expected before such feedback can be acted upon.

It is quite obvious that on a worldwide basis, there is a demand for new methods which are practical, expedient, economical and reliable as far as inspecting the degree of purity of components is concerned, a specific requirement being differentiating among areas, zones and portions of the product; another requirement is quantification. Sectionalizing involves particularly sections or portions of limited length as far as continuous casting is concerned. It is believed that the present invention meets all these requirements and constitutes a significant improvement over the art.

The following is a summary of known test methods concerning impurities. One method includes the extraction of sulphur, also known as the Bauman print method. Metallography as per a German standardized iron test sheet for steel 1570. Step turning samples being another kind of test set forth under the number 1580. There are also known so-called blue-fracture samples; ultrasonic testing of plate-stock even if entirely along the edges, a slime extraction method, i.e. a certain residue is isolated; and quantitative metallography on relatively large plate stock areas such as areas of 200 cm². It is beyond the scope of this discussion to detail a critique on these methods. Generally however, it can be said that as far as the present trend towards enhancing the testing degrees of impurities is concerned, these methods are no longer adequate. Owing to a clear lack of suitable pieces of equipment the problem was posed for many years that it was very difficult, even impossible, to determine by way of testing whether any particular feature used in the making and processing of steel, did or did not exhibit the desired result, except that much later when failure rates, or lack of them, became known.

DESCRIPTION OF INVENTION

It is an object of the present invention to provide a new and improved method for the manufacture of samples to be used in ultrasonic test operations for purposes of highly accurately determining the degree of purity of the metal in the sample, so that the determining can be immediately and directly made upon a given product.

It is a particular object of the present invention to provide a new and improved method for the making of samples for ascertaining impurities in metals including steel, with emphasis on continuously cast steel.

In accordance with the preferred embodiment of the present invention, it is suggested to cut a sample from a product, either a continuous cast one, or one product which has already undergone additional deformation, with the proviso that this sample is to have at least a ten-fold thickness of the minimum pre-thickness needed or desired for ultrasonic investigation, and that the thickness dimension of the sample runs in a plane parallel to the axis of casting, or the directon of main deformation of the product being tested, and having plane parallel cutting surfaces transversal to that thickness extension, and that the sample is heated as high as possible (non-melting being assumed) and is then deformed transversally to that thickness extension, down to the desired thickness needed for ultrasonic testing.

The crux of the invention is to concentrate inclusions and impurities in particular zones so that on the one hand there is a well-defined local enrichment in impurities and inclusions, which then permits, on a statistical basis, a rather definite conclusion about the degree of overall purity of that product in general, including particularly, casting ingots, so that owing to the increase in density, the degree of purity and overall evaluation on a statistical basis including continuous casting and such, is now made possible. Thus concentrating begins with the fact that impurities are flushed up in a cast product. Then the pre-sample is taken and then impurities are concentrated what was originally (on casting) in a horizontal stretch until a thin vertical dimension. That sample is then rolled to concentrate that horizontal stretch (upsetting) in one direction. That direction is in casting direction in FIG. 1 and others are peripherally shown in FIG. 8.

DESCRIPTION OF THE DRAWINGS

While the specification concludes withh claims particularly pointing out and distinctly claiming the subject matter which is regarded as the invention, it is believed that the invention, the objects and features of the invention, and further objects, features and advantages thereof will be better understood from the following description taken in connection with the accompanying drawings in which:

FIG. 5 is micrograph showing distortion and destruction of an inclusion;

FIG. 9 shows an oval sample from an unknown product;

The invention is first explained with reference to a particular example having to do with a round made by continuous casting of steel. Here it assumed that all inclusions of a sample of 25 kg are concentrated in a relatively small sample and test sheet for purposes of ultrasonic testing. As shown in FIG. 1a, a sample in the form of cylinder (175 diameter, 120 axial length) is rolled flat to have the configuration of a surfboard or oval which is shown in FIG. 1b. The directions of rolling are transverse to the axis of the round as it was cast which is perpendicular to the plane of the drawing. The curved strand is stretched from the underside to the upper side U whereby reference numeral W 11 indicates the direction of rolling. The direction WR1 indicates subsequent stretching. An inclusion ribbon band 10 of impurities is predominantly located near the upper side U of the presample and, of course, of the entire product. These inclusions are upset by the rolling. The high particle density per volume remains.

As a final result (oval FIG. 1b) clean and dirty zones are rather very neatly separated in this manner as a preparation for ultrasonic testing, which means that unnecessary "chaf" for the test is discarded. The inclusions are stretched as well as widened, thereby resulting in the sample becoming sensitized as far as ultrasonic testing is concerned.

In spite of a sufficiently pronounced degree of deformation, the sheet-stock thickness (1.12 mm) of the sample is not made to drop below a critical level for ultrasonics. Thus, by way of example, a disc cut of a round at 175 mm and 120 mm axial length was flattened to the surfboard configuration of 875 mm length a shaft axis of 350 mm. The original thickness of that disc was 120 mm and is now reduced to 12 mm.

Figure 2:
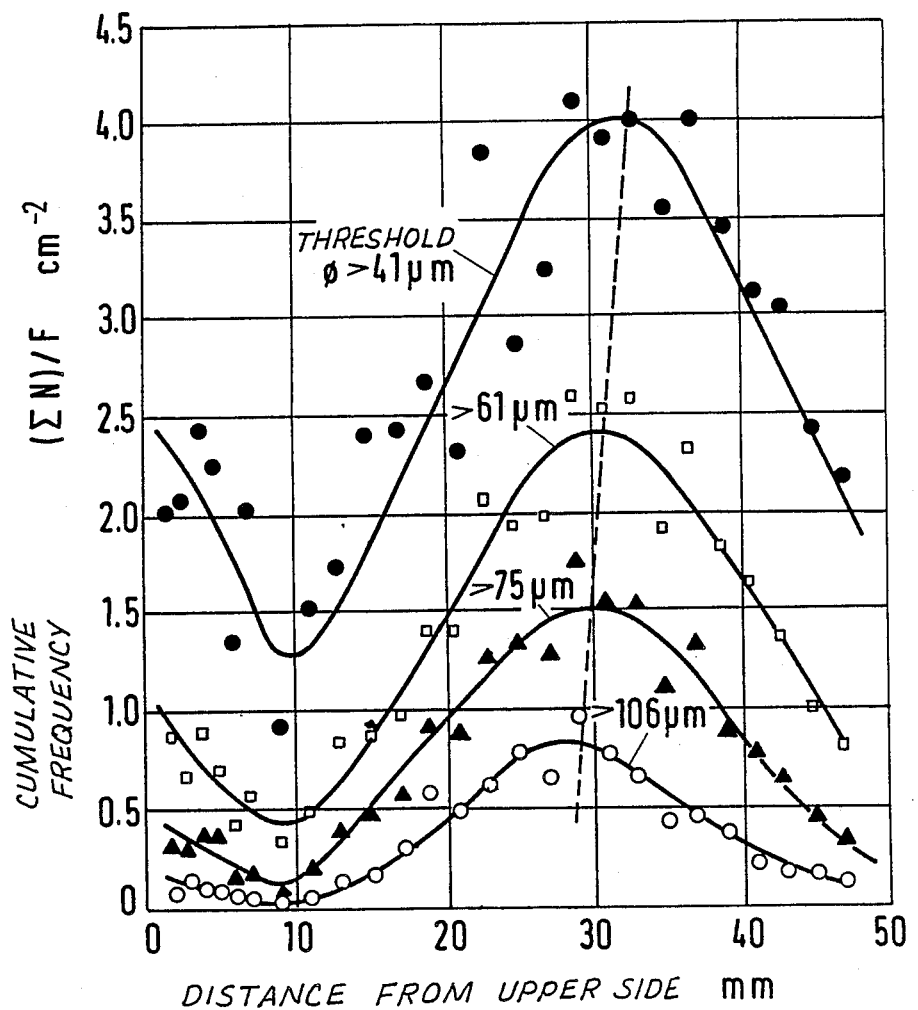
FIG. 2 and FIG. 3 are plotted statistical data in distance versus frequency from the upper side and the lower side of the product.

FIG. 2 illustrates a spectrum and size distribution of the inclusions on this thus defined upper side (band 10) of a round in which impurities have been accumulated. For symbol explanation see FIG. 4. One can say that rolling temperature is the parameter.

Figure 3:
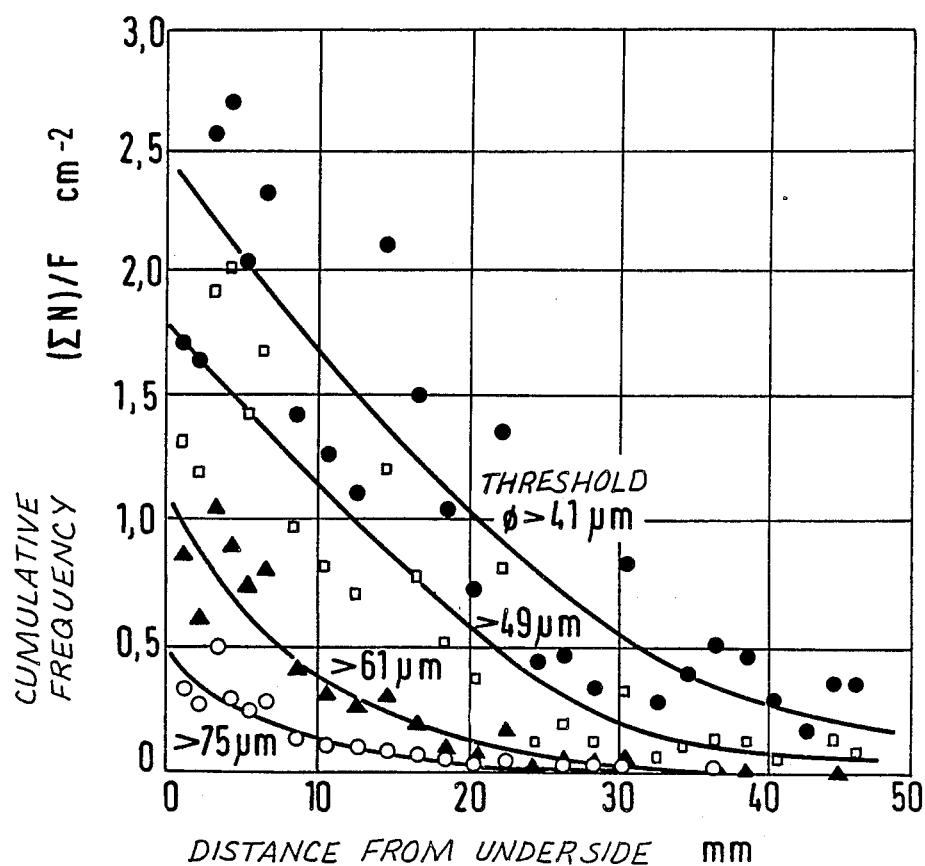

FIG. 3 is a corresponding diagram but shows the distribution near the "clean" underside L. Owing to these investigations conducted by the applicants for purposes of determining deformability of inclusions in steel, it was readily determined that for attaining the goal of the invention to use as high a rolling temperature s possible, such as 1350 degrees centigrade.

Figure 4:
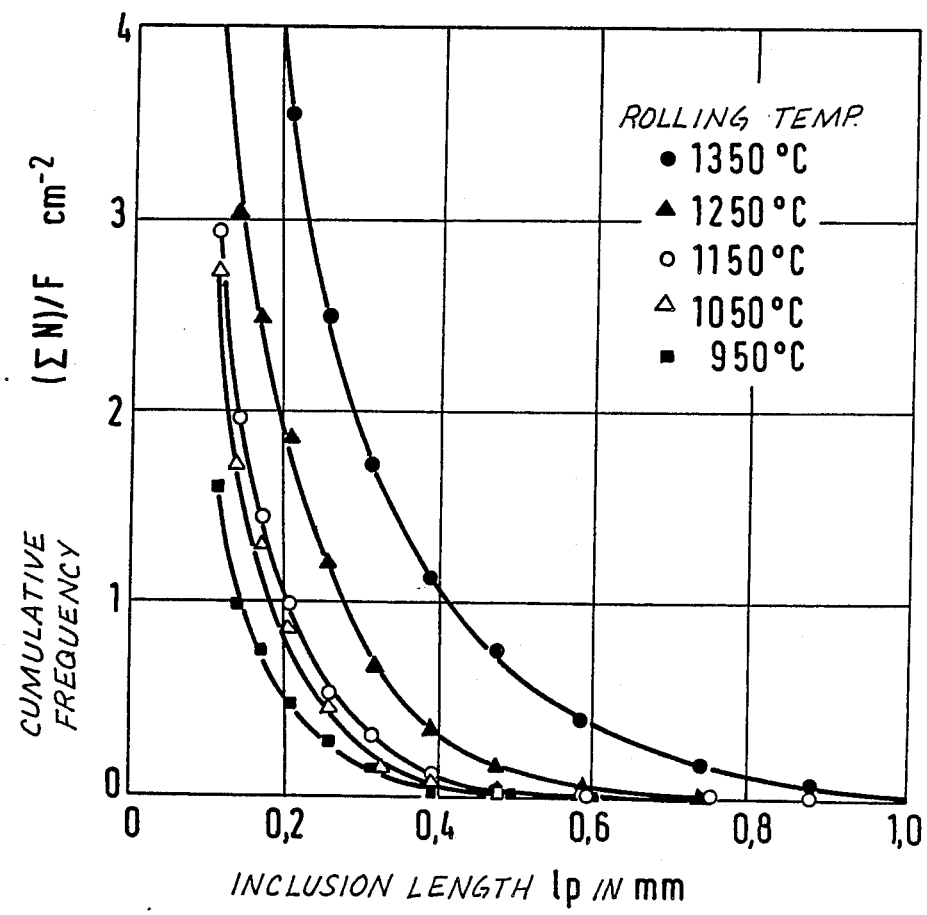
FIG. 4 is a plot in which statistical data is plotted against the length of stretched inclusions.
Figure 6A:
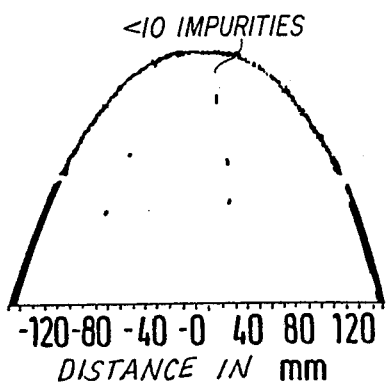
FIG. 6 shows a classification scheme of samples regarding different degrees of purity.
Figure 6B:
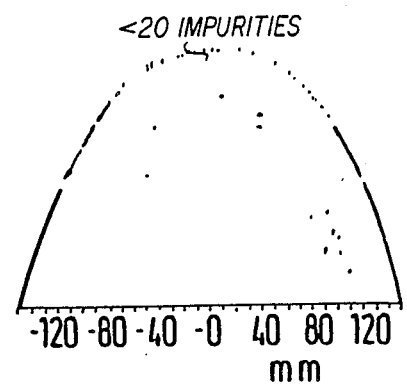
Figure 6C:
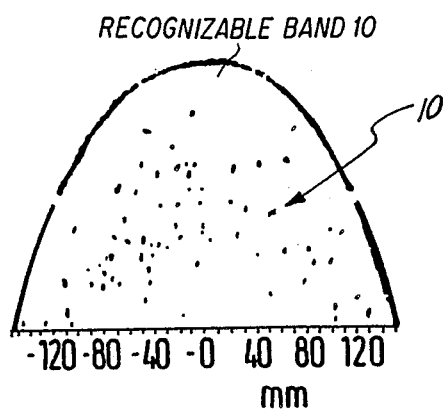
Figure 6D:
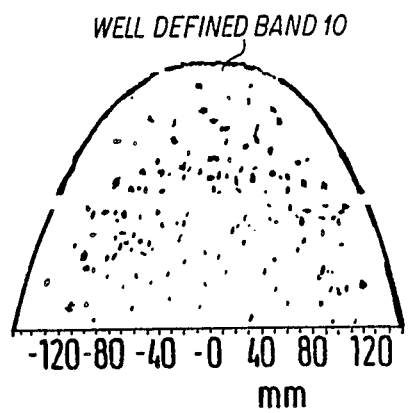
Figure 6E:
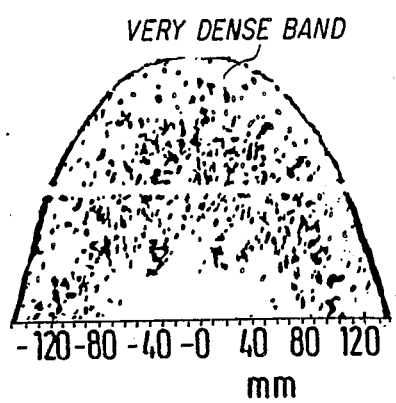
Figure 6F:
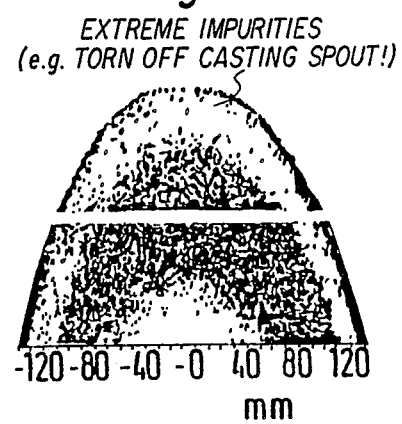

FIG. 4 illustrates the inclusions which originally had a more or less spherical configuration but which, with increasing rolling temperature, are stretched to an increasing extent. This is what is meant by "inclusion length" of the impurities.

FIG. 5 now shows how a basically elliptically configured inclusion is deformed on rolling, the illustration being in a plane parallel to the direction of rolling. In fact, the inclusion has been destroyed, but its originally elliptical contour is still recognizable.

FIG. 6, including part 6A-6F, illustrates several types of examples, i.e. ultrasonically tested samples of the surfboard or oval configuration; they have been organized in this FIG. 6 in accordance with a certain classification. These examples are real and the classification is metallurgically justifiable. For purposes of comparison, it should be mentioned that the Bauman print does not differentiate among these various cases. In a concrete case of the sample with a Class 6, the S-discharge was almost white, while the emulsified casting slag was obviously not covered by the S-discharge. The development of the test program works as follows.

Samples of a castround are plane-parallel cut or burned in cylinders of 130 mm lengths, measured in the direction of casting. The upper side of casting (physically) is then identified by means of certain markings left by certain withdrawal rollers. The underside is thus defined simply by being the opposite side, and is notched by a 10 mm length cut. This cut serves for orienting the roll.

Figure 1:
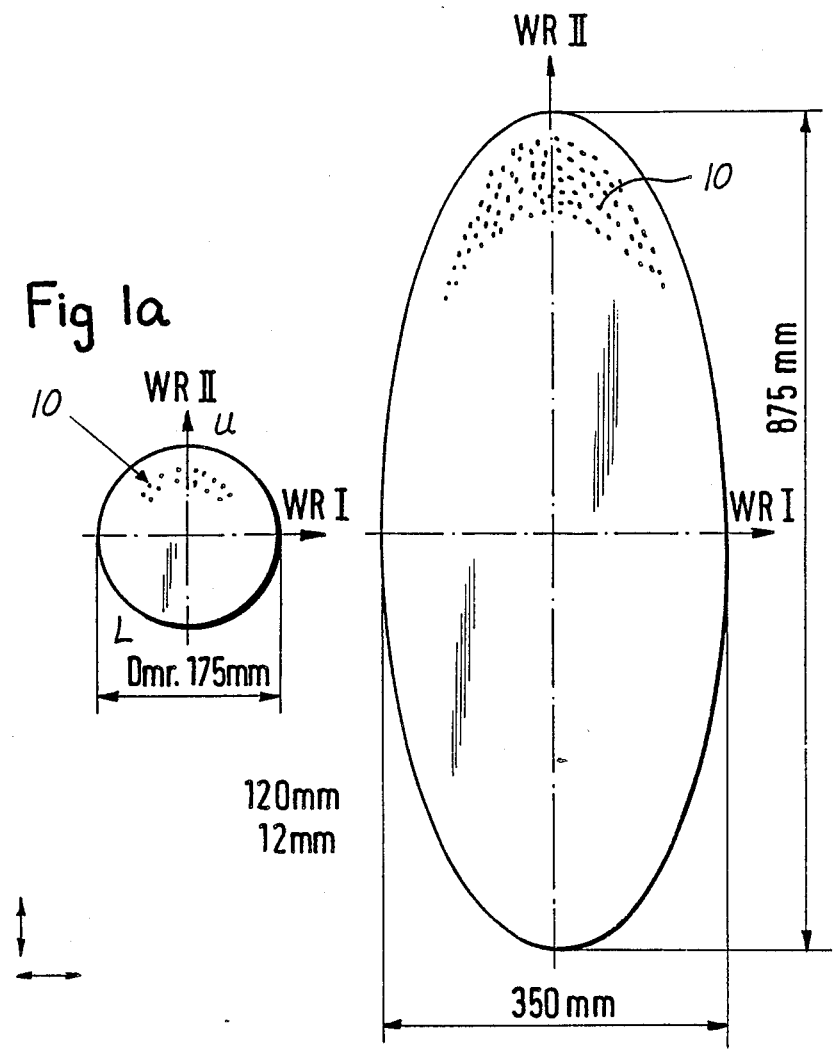
FIG. 1a and 1b illustrated version of a pre-sample and a coupled sample showing also representative diameters.

These round samples are now heated to a temperature of 1350 degrees, and in a rolling stand the following program for roll direction WRI-FIG. 1a,b is provided: 130, 120, 105, 80, 70 and 60 mm. Readily now this elliptically deformed sample is turned by 90 degrees and is stretched in the following passes identified above by WRII; 48, 36, 18 and 13 mm. The position of the notch is a good indicator about how symmetrically one did roll. The elliptically contoured ovals or surfborads are then sawed and partitioned.

As far as the upper side is concerned, two 100 mm wide strips are cut from the apex of the ellipse. As far as the underside is concerned, it is sufficient to have a strip extracted just for purposes of verification, calibration and reference. This is sufficient in order to determined that in fact what is deemed upper and under side are properly so designated and there was no mix-up prior to rolling. The three samples are now plane parallel ground and cut and tested in a suitable ultrasonic test stand such as a HIC apparatus.

The invention now uses the fact that in the case of curved continuous casting, inclusions are basically on the upper side, that is the inside of the curve. As far as horizontal casting is concerned, this phenomenon is even more pronounced; basically it is quite independent from the contour and cross-section of the casting.

Figure 7:
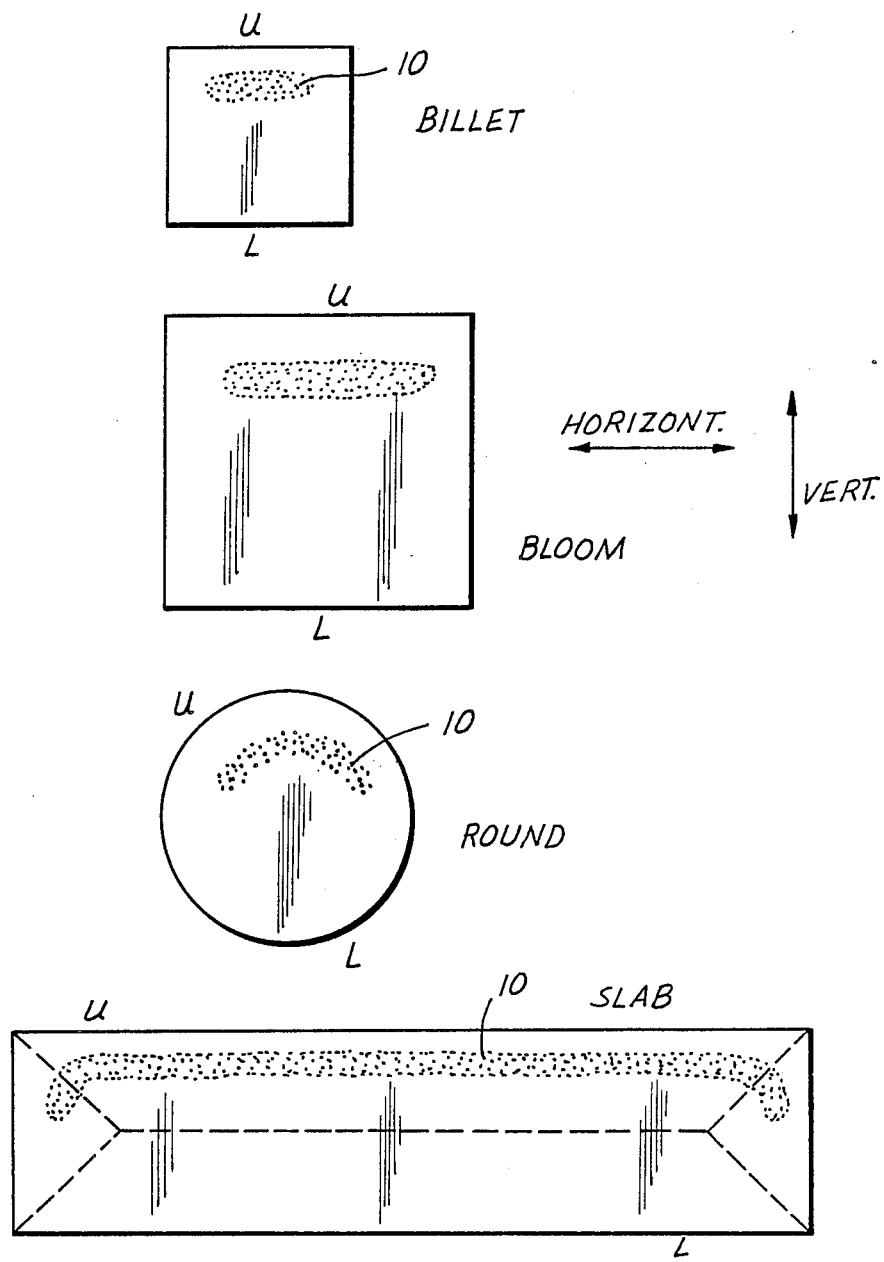
FIG. 7 shows in four diagrams cross-sections through billets, blooms, rounds and ingots demonstrating the inclusion of impurity bands.

FIG. 7 shows the position of the inclusion band in various products that have been made by casting. Inclusions are predominantly found for various kinds of rolled products such as billets, blooms, rounds and slabs. Upon suitably rolling certain sections with upsetting of that portion in the product which predominantly contains the inclusions, one can in fact produce a suitable test-sheet in which the inclusions are indeed concentrated, and owing the particular rolling, they are in effect sensitized. It may be assumed that the direction of upsetting runs parallel to the direction of casting, but that is not essential. With reference to the orientation of the casting, upsetting may occur horizontal transverse to the cast product.

In the case of narrow sides of the ingots, the direction of upsetting may even be vertical, which is however, mentioned here only for purposes for completion, because this kind of approach, though conventional, does not promise the largest possible effect, and may in effect exhibit certain undesirable results analogous to conventional edge-zone testing.

Now from this product, suitably rolled pieces can be cut through sawing. The sample thickness is transverse to the plane of the drawing of FIG. 7. Moreover, it is assumed that a tenfold thickness reduction is desirable simply to enhance sensitivity as far as the detection of inclusions is concerned. The test-sheet, moreover, should not be thinner than 10 mm, which for steel is about the minimum for ultrasonic testing. It should be realized that for ultrasonic testing, the first millimeter thickness or so of a product, i.e. a surface-near region, is not really tested. As far as the initial thickness of a cut sample is concerned, there is no basic principle limit, the limit being simply given by local rolling facilities.

Figure 8A:
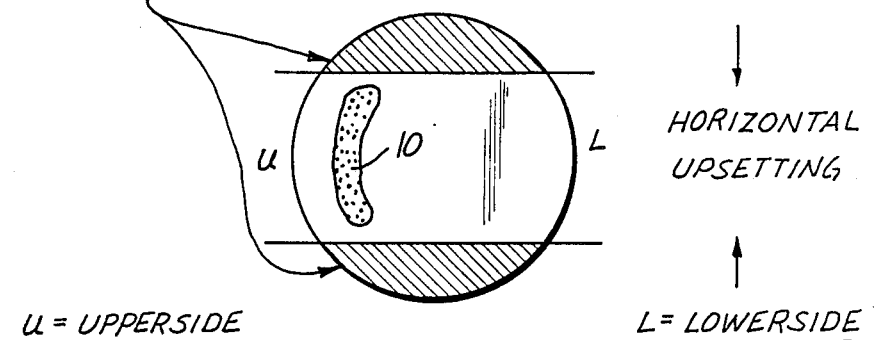
FIG. 8, in parts a and b illustrates the process of practicing the invention by deforming the preliminary sample transversely to a long extension of the impurity band.
Figure 8B:
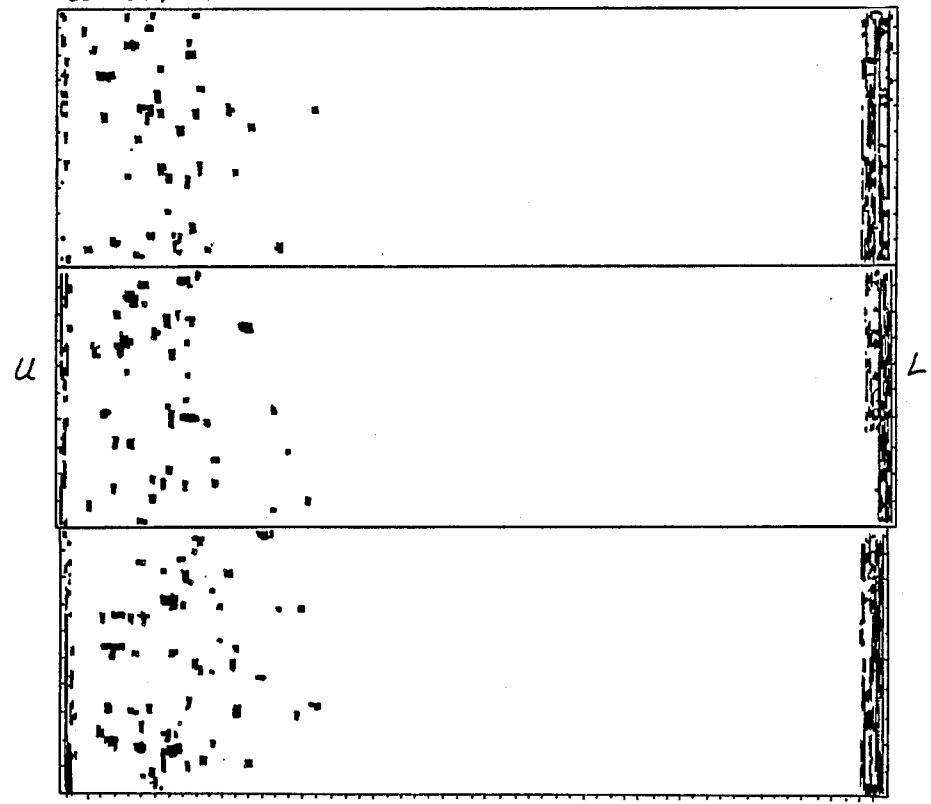

Concerning FIG. 8, horizontal upsetting of the inclusion band is explained; particularly in the case of a round sample (having been turned by 90 degrees); the upsetting is carried out by a roll parallel as well as perpendicularly to the direction of casting (FIG. 8a). The direction of casting is transverse to the plane of the drawing of FIG. 8a. Prior to rolling, side segments of the round cross-section are cut off, so that the no longer round glide stock can lie flat and is introduced into the rolling gap in a controlled fashion. Rolling was in FIG. 8a from left to right or vice versa and transverse to the plane of the drawing. FIG. 8b now shows the flat rolled piece with upsetting having occurred transversely to the plane of FIG. 8b irrespective of the direction of rolling. The ultrasonic test, to the extent it can be seen in FIG. 8, is indeed a verification of the applicability of this kind of roll for the inventive purpose. If the previous sawing is inaccurate, i.e. not exactly at an angle of 90 degrees to the inclusion band 10 of impurities, then the ultrasonic indication does reach the edge of the sheet stock.

The invention can be used particularly to test continuous cast material of unknown origin, but prior to the test, one can determine what was the upper and what was the under side. The method which was explained above and once this orientation has been made, the degree of purity of the material can be determined. A supplier of raw products may for example, be assumed to have manufactured by way of a curved continuous strand or ingot having dimensions of 360 mm by 420 mm which are then to be changed by rolling into hollows of 177 mm diameter. Pickling a dS-extraction does not provide adequate information. 177 mm diameter material is notched arbitrarily on two spots of the surface, and is then rolled into a "surfboard", i.e. an oval.

Figure 10:
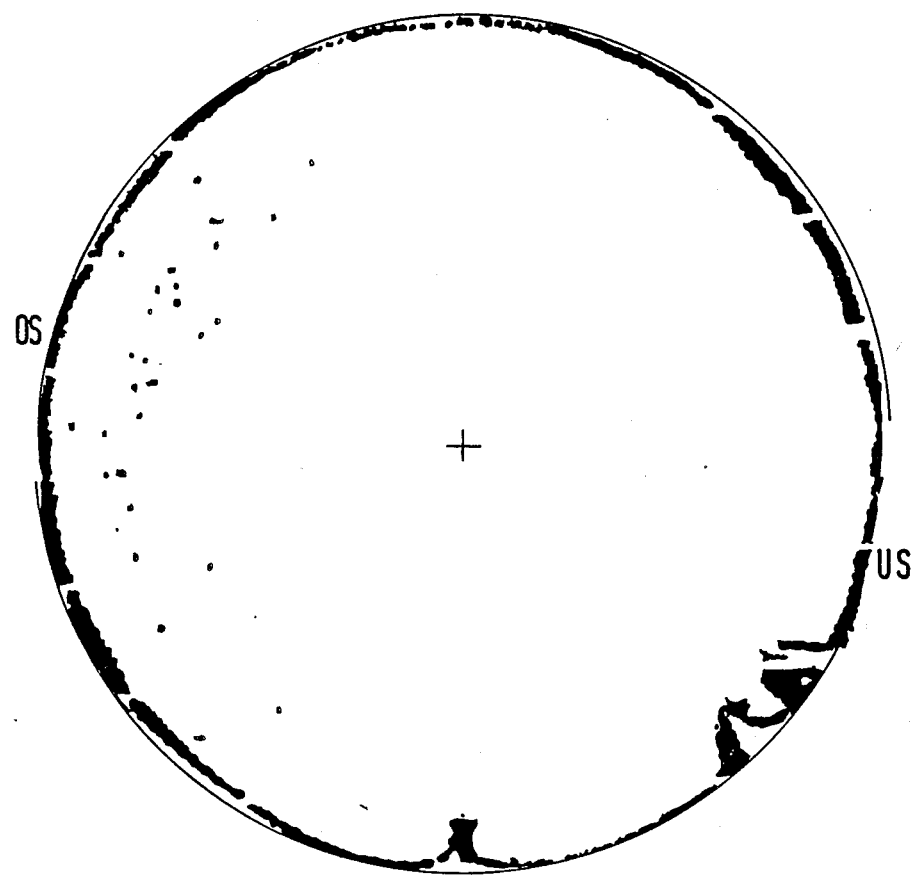
FIG. 10 is a diagram for retransforming the sample of FIG. 9.

FIG. 9 illustrates the result of ultrasonic testing that sample. As far as the ellipse is concerned, one provides mathematically as retransformation to the round material, and that is found in FIG. 10. Now the direction and orientation of casting upper side and casting under side is determined. Folowing this, other 100 mm round samples will be processed with knowledge of that particular orientation, and they are then investigated and inspected with regard to any impurity. Actually by this method one can subseqently distinguish ordinary block casting from continuous casting in and along a curved method. It must be mentioned that after some kind of deformation, this distinction has normally been almost impossible.

Figure 11:
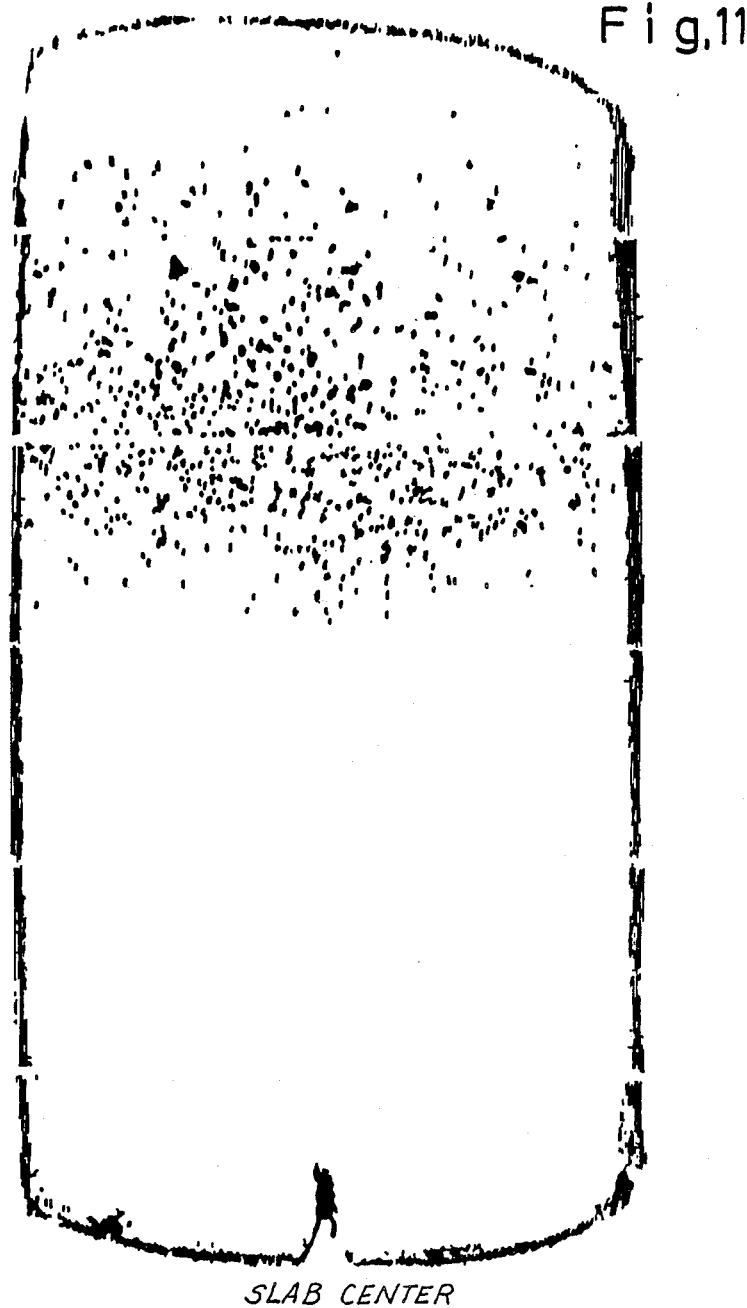
FIG. 11 shows a ultrasonic test sample of a sample take from the upper middle of a slab ingot.

FIG. 11 shows how the invention is applied to a slab ingot made by continuous casting. It is assumed that the so-called S-sample-taking did not indicate any particularly poor grading. The figure shows the ultrasonic test results from the upper slab surface near the middle therein. The lower part towards the slab center was free from any indication. The analized sample was roughly at one half of the slabingot width.

Figure 12:
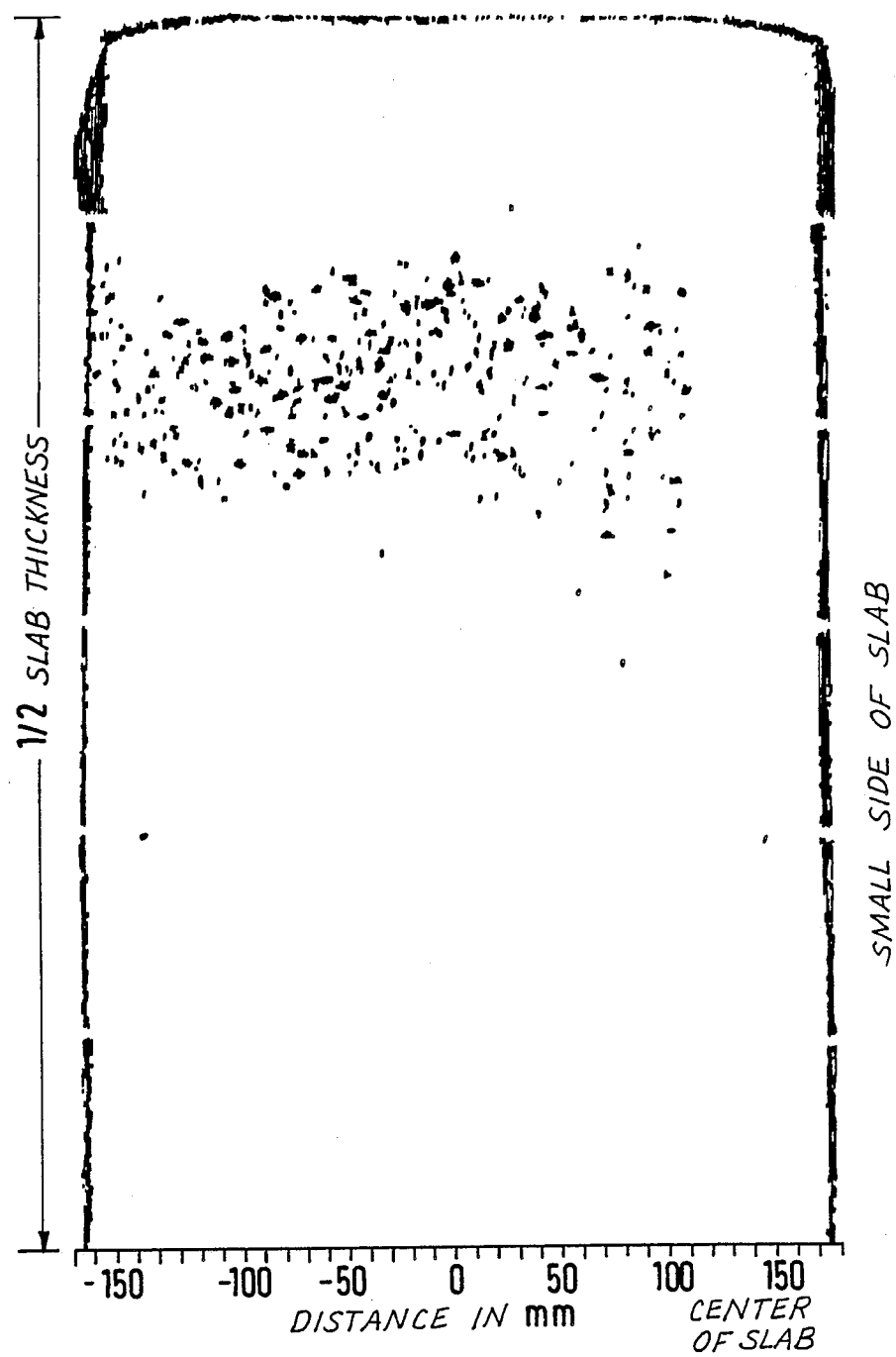
FIG. 12 is a similar test diagram taken from the small side of a slab ingot.

FIG. 12 shows how, in an entirely different slab ingot, the area of the narrow or small side was tested. Here one sees a particular layer which entirely free from any inclusion Both illustrated samples are then, just as in the case of standard rolling of round material, widening it to a two-fold value and stretching it to a five-fold value. For the exact ascertainment of distances, thickness, and so forth, particularly involving the inclusions band, one had to retransform mathematically from the sheet to the initial product. This, however, was not done in this case.

The invention is also applicable to so-called thin-wall products such as tubes or sheets of cross-sections with a diameter of less than 100 mm, or with edge-length which in accordance with the slimness cannot be subject to upsetting in the directing of length extension as far as the sample is concerned, because under pressure the sample will simply buckle.

In this case, then, the sample can be processed as follows. For example, several sheets are bundled and mechanically held together, or in the case of tubular samples, one simply inserts a suitable core, or in the case of thin rods, one provides a tubular sleeve. In all these cases, one establishes a sample which will not kink, or bend, or buckle. The auxiliary element will be also deformed but does not structurally combine with the desired product, and can simply be separated therefrom.

The invention is not limited to the embodiments described above; but all changes and modifications thereof, not constituting departures fromthe spirit and scope of the invention, are intended to be included.

We claim:

1. Method for making a sample for ascertaining impurities in metal products, particularly steel products made by continuous casting, comprising the steps of:

cutting a preparatory sample from the object to be tested which has at least a ten-fold thickness of the sample thickness for comfortably providing ultrasonic testing;

the thickness dimension of said preliminary sample extends in a plane parallel to the direction of casting and/or to the main direction of immediately preceding deforming, there being plane parallel cutting surfaces at right angles to said thickness dimension;

heating said preliminary sample to a comparatively high deforming temperature; and deforming that sample by reducing said preliminary sample transversally to the thickness dimension to a desired sample thickness.

2. Method as in claim 1, said preliminary sample being provided with a marking indicating its length extension.

3. Method as in claim 2, providing a marking on the underside for the preliminary sample taken from a casting that was made by curved continuous casting.

4. Method as in claim 2, including the step of cutting a strip-like sample from the side opposite the marked side.

5. Method as claim 1 wherein said preliminary sample is rolled transversally to the extension of the thickness dimension in the direction of a line that runs from the initial upper side of casting to the lower side thereof.

6. Method as in claim 1, said deforming by rolling is carried through the following steps: rolling the preliminary sample transversally to a thickness extension and repeated in the same direction until the thickness has been reduced to about half the initial value;

turning the thus-treated product by 90 degrees within the plane of rolling;

rolling the thus-turned preliminary sample in the same direction as far as rolling is concerned until about one-tenth of the initial thickness obtains; and separating a strip-shaped sample for ultrasonic testing from the resulting sheet-stock.

7. Method as in claim 6, wherein for samples taken from a product with round cross section, the preliminary sample is taken from an apex region of the long axis.

8. Method as in claim 1, the temperature exceeding 1100 degrees C.

9. Method as in claim 7, the temperature being about 1350 degrees in the case of steel.

10. In a method of ultrasonic testing, a preparatory method of making a sample for ascertaining impurities in cast steel products, the impurities accumulating in particular strata having a horizontal extension corresponding to the configuration of the product, and a reduced thickness dimension in the vertical, comprising the steps of:

cutting a preparatory sample from said object such that the thickness dimension for the US test method will be in one direction in the horizontal;

heating said preparatory sample; and reducing this prospective thickness dimension to thereby compact impurities of said band and increase the density distribution of the compacted impurities.

11. Method as in claim 10, wherein a transverse, horizontal direction is a direction of continuous casting, the reducing step is a rolling step transversely to said direction.

12. Method as in claim 10 wherein said direction is a direction of continuous casting the product, the reducing step is a rolling step or steps carried out transversely to said direction.

13. Method of ultrasonic testing a sample to be taken from a continuous cast product, comprising the step of:

taking a sample from the product in what has been an upper region during casting;

compacting impurities in said sample by way of rolling the sample, the compacting to occur in a direction in or transverse to the direction of casting, in either case the direction being horizontal with reference to the orientation of the sample before being taken from the product and during casting; and providing ultrasonic testing in said direction of compacting.

14. Method as in claim 13, including the step of heating the sample before the rolling to about 1350 degrees C.

15. Method as in claim 13, the rolling being carried out in two orthogonal directions, both perpendicular to the direction of compacting.

* * * * *